United States Patent [19]

Doyle

[11] 4,319,050

[45] Mar. 9, 1982

[54] COPPER COMPLEX AS CATALYST FOR FORMATE ESTER DECARBONYLATION

[75] Inventor: Gerald Doyle, Whitehouse Station, N.J.

[73] Assignee: Exxon Research & Engineering Co., Florham Park, N.J.

[21] Appl. No.: 234,161

[22] Filed: Feb. 13, 1981

[51] Int. Cl.$^3$ .................. C07C 41/01; C07C 31/04
[52] U.S. Cl. .................... 568/671; 568/626; 568/635; 568/659; 568/715; 568/716; 568/876
[58] Field of Search ............... 568/626, 635, 659, 671, 568/715, 716, 876

[56] References Cited

U.S. PATENT DOCUMENTS 3,812,210  5/1974  Higdon et al. ............... 568/671 X
4,262,157  4/1981  Hori et al. .................. 568/671 X

OTHER PUBLICATIONS

Tsuji and Ohno, International Methods in Synthetic Organic Chem., 1, 157 (1969).
Halpern and Kemp, J. Am. Chem. Soc., 88, 5147 (1966).
Coffey, Chem. Comm., 923 (1967).
Pignolet and Doughty, J. Am. Chem. Soc., 100, 7083 (1978).
Ying and Madix, J. of Catalysis, 61, 48 (1980).

*Primary Examiner*—Howard T. Mars
*Attorney, Agent, or Firm*—James H. Takemoto

[57] ABSTRACT

A homogeneous catalytic process for the decarbonylating of formate esters to alcohols and carbon monoxide. The process comprises contacting formate esters of the formula HCOOR where R is $C_1$–$C_{10}$ aliphatic, $C_7$–$C_{14}$ araliphatic or $C_6$–$C_{10}$ aryl with a copper complex of the formula Cu(L)X where L is CO, phosphine or phosphite and X is the anion of an acid in an inert atmosphere at temperatures of from about 100° to 300° C.

16 Claims, No Drawings

COPPER COMPLEX AS CATALYST FOR FORMATE ESTER DECARBONYLATION

BACKGROUND OF THE INVENTION

This invention relates to the decarbonylation of formate esters. More particularly, formate esters are decarbonylated to alcohols in the presence of a copper complex.

Decarbonylation reactions, i.e., the removal of carbon monoxide from organic carbonyl compounds, have been reviewed by Tsuji and Ohno, International Methods in Synthetic Organic Chemistry, 1, 157 (1969). Rhodium complexes can be used to convert aldehydes and acyl halides to alkanes and alkyl halides or olefins, respectively. Ruthenium complexes can also be employed for the decarbonylation of aldehydes. These reactions generally involve more complex carbonyl compounds with relatively high molecular weights as compared to simple compounds such as formaldehyde and acetaldehyde, and are typically stoichiometric in nature. Decarbonylation reactions are catalyzed by palladium metal on a support. Halpern and Kemp, J. Am. Chem. Soc., 88, 5147 (1966), report that formic acid will react with ruthenium (II) chloride in a stoichiometric decarbonylation reaction. Coffey, Chem. Comm. 923 (1967), reports that phosphine stabilized iridium and ruthenium complexes are excellent homogeneous catalysts for the decomposition of formic acid. The reaction, however, results in decarboxylation rather than decarbonylation under catalytic conditions. Pignolet and Doughty, J. Am. Chem. Soc., 100, 7083 (1978), studied the mechanism of the homogeneous catalytic decarbonylation of benzaldehyde and heptanal using rhodium complexes containing chelating phosphine ligands. Finally, Ying and Madix, J. of Catalysis, 61, 48 (1980) investigated the decarboxylation of formic acid with a metallic copper catalyst.

There is considerable interest in the selective preparation of low molecular oxygenates from synthesis gas. In practice, however, a range of products is usually obtained. Therefore, flexibility in the interconversion of products, i.e., the conversion of less valuable products to those of greater economic impact, is desirable. Within the scheme of interconvertibility of low molecular weight oxygenates, it would be useful to have a means of decarbonylating formate esters such as methyl formate.

SUMMARY OF THE INVENTION

It has been discovered that the decarbonylation of formate esters to produce alcohols and/or ethers and carbon monoxide can be accomplished catalytically with copper complexes. Accordingly, the present process for the homogeneous decarbonylation of formate esters of the formula HCOOR where R is $C_1$–$C_{10}$ aliphatic, $C_7$–$C_{14}$ araliphatic or $C_6$–$C_{10}$ aryl comprises contacting the formate ester with a copper complex of the formula Cu(L)X where L is CO, phosphine or phosphite and X is the anion of an acid in an inert atmosphere at temperatures of from about 100° to 300° C.

The present copper complex catalysts for formate ester decarbonylation are less expensive and more efficient than known homogeneous catalysts for the decarbonylation of higher molecular weight aldehydes. Catalyst losses and recovery procedures are serious problems with noble metal catalysts but much less so with copper based catalysts.

DETAILED DESCRIPTION OF THE INVENTION

Formate esters can be converted to alcohols and carbon monoxide. The conversion of formate esters is described by the following reaction scheme:

$$\text{HCOOR} \xrightarrow[\Delta]{\text{[Cu Cat]}} \text{ROH} + \text{CO}.$$

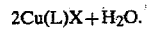

Some alcohol may then be converted by dehydration to the corresponding ether, i.e., ROR, resulting in an alcohol/ether mixture as final product. Copper catalysts have the formula Cu(L)X where L is CO, phosphine or phosphite for the formula $P(R')_3$ or $P(OR')_3$ where $R_1$ is independently H, $C_1$–$C_{10}$ alkyl, $C_7$–$C_{14}$ aralkyl, $C_3$–$C_8$ cycloalkyl or $C_6$–$C_{10}$ aryl, preferably CO or $P(OR')_3$ and X is preferably the anion of a strong inorganic or organic acid. Examples of anions include halide, sulfate, nitrate, phosphate, trihaloacetate, oxalate, p-toluene sulfonate, trifluoromethylsulfonate and the like, with $CF_3SO_3^-$ and $CH_3C_6H_4SO_3^-$ being especially preferred. Examples of copper catalysts include Cu(CO)Cl, $Cu(CO)NO_3$, $Cu(CO)CF_3COO$, $Cu(CO)CF_3SO_3$, $Cu(CO)CH_3SO_3$, $Cu(CO)CH_3C_6H_4SO_3$, $Cu(P(OCH_3)_3)CF_3SO_3$, $Cu(P(OC_6H_5)_3)CF_3SO_3$, $Cu(P(OCH_2C_6H_5)_3)CH_3C_6H_4SO_3$, $Cu(P(C_6H_5)_3)_3CH_3C_6H_4SO_3$, $Cu(P(Bu_3)_3)Cl$ and $Cu(PC_2H_5(C_6H_5)_2)CF_3SO_3$. Preferred catalysts are $Cu(CO)CF_3SO_3$, $Cu(P(OCH_3)_3)CF_3SO_3$, $Cu(P(OC_6H_5)_3)CF_3SO_3$ and $Cu(CO)CH_3C_6H_4SO_3$. The copper catalysts may be prepared according to the reaction $Cu_2O + 2L + 2HX$ $$2Cu(L)X + H_2O.$$

Formate esters have the formula HCOOR where R is preferably $C_1$–$C_{10}$ alkyl, $C_7$–$C_{12}$ aralkyl or phenyl more preferably $C_1$–$C_6$ alkyl, and especially methyl or ethyl. Decarbonylation of methyl formate results in methanol or methanol/dimethyl ether mixtures.

In the decarbonylation of formate esters, iodides may be added as promoters. Examples of suitable iodides include iodine, HI, alkali metal iodide, alkaline earth metal iodide, substituted and unsubstituted ammonium or phosphonium iodides, and organic iodides. The ammonium or phosphonium iodides have the formula $N(R^2)_4I$ or $P(R^2)_4I$ where each $R^2$ is independently hydrogen, alkyl, aralkyl or aryl, preferably $C_1$–$C_{10}$ alkyl, $C_6$–$C_{10}$ aryl or $C_6$–$C_{12}$ aralkyl. Organic iodides are preferably $C_1$–$C_{10}$ aliphatic iodides with $C_1$–$C_6$ alkyl iodides being more preferred. Methyl iodide is especially preferred.

Catalyst concentration may vary widely and ranges from about 0.0001 to 1 wt. % Cu calculated as metal and based on the reaction mixture, preferably 0.001 to 0.5 wt. % and especially 0.01 to 0.05 wt. %. The amount of iodide promoter is not critical and may range from an I:Cu ratio of 1:10 to 10:1, preferably 1:1 to 10:1.

The reaction is preferably run with formate ester as the only solvent present. Other organic solvents which are inert under reaction conditions may be present, if desired. Examples of such solvents include hydrocarbons, ethers, ketones, other esters, and halogenated hydrocarbons.

Decarbonylations according to the invention may occur at temperatures of from 100° to 300° C., preferably 150° to 250° C. and especially 175° to 220° C. Lower temperatures generally require longer reaction times whereas higher temperatures may result in catalyst instability and increased by-product formation.

The reaction takes place in an inert atmosphere. Oxygen and water vapor may be harmful due to possible oxidation of Cu(I) in the complex to Cu(II). Any inert gas or gas mixture is suitable, e.g., carbon monoxide, nitrogen, noble gases, and the like, preferably carbon monoxide. Gas pressures may range from 0.1 to 100 MPa, preferably 0.2 to 2 MPa (1 MPa≅10 atm.). There is generally no need to run the reaction at higher pressures (>2 MPa). Reaction times may range from 1 to 24 hours, preferably from 1-6 hours.

The process may be operated in a continuous or batchwise mode, preferably continuously. In continuous operation, unreacted formate esters is separated and recycled back to the reactor vessel.

By practicing the process according to the invention, formate esters can be catalytically converted to alcohols and/or ethers using an inexpensive catalyst with relatively high efficiency. The selectivity to alcohols and/or ethers as final products can be controlled by varying the nature of the copper complex used as catalyst and the reaction conditions. Formate esters are a typical by-product of the preparation of methanol, ethanol, acetaldehyde and the like from synthesis gas.

EXAMPLE 1

A 1-liter high pressure stirred autoclave equipped with a catalyst blowcase was charged with 300 ml methyl formate, 50 ml toluene as an internal standard and 1.42 grams methyl iodide. The autoclave was flushed with CO then sealed and pressurized with 1 MPa CO. The vessel was then brought to 220° C. and a solution containing 0.48 g $Cu(CO)CF_3SO_3$ in 100 ml methyl formate was pressurized into the reactor with CO. This mixture was allowed to react with constant stirring for 1 hour with liquid samples being withdrawn at appropriate intervals for analysis and a gas sample taken at the conclusion of the reaction. Both gas and liquid samples were analyzed by gas chromatography. A sample taken at one hour indicated a conversion of methyl formate of 26% with a selectivity to methanol of 55% and to dimethyl ether of 45%. Only traces of $CO_2$ were detected in the gas sample.

EXAMPLE 2

An experiment identical to that described in example 1 was carried out except that no methyl iodide was used. In this case the liquid sample taken at one hour indicated a methyl formate conversion of 19%. The selectivity to methanol was 55% and to dimethyl ether 45%. These examples show the beneficial effect of methyl iodide on methyl formate conversion without any alteration in product selectivity.

EXAMPLE 3

This example is identical to example 1 except that the reaction was run for 2 hours. In this case the analysis of the two-hour sample indicated a conversion of methyl formate of 40% and a selectivity to methanol of 48% and to dimethyl ether of 52%.

EXAMPLE 4

Example 3 was repeated except that 0.37 g $Cu(CO)CH_3SO_3$ was used as a catalyst in place of the $Cu(CO)CF_3SO_3$. An analysis of the two-hour sample indicated a methyl formate conversion of 2% with methanol being the only detectable product.

EXAMPLE 5

The procedure of example 3 was followed except that 0.56 g $Cu(CO)(CH_3C_6H_4SO_3)$ was used in place of the $Cu(CO)CF_3SO_3$ and the reaction was carried out for 4 hours. The conversion of methyl formate was 10% with methanol being the major product. Only traces of dimethyl ether were detected.

EXAMPLE 6

This example is identical to example 5 except that 1.67 g of $Cu[(C_6H_5O)_3P]CF_3SO_3$ was employed as a catalyst. The four-hour liquid sample indicated a conversion of methyl formate of 38%. The selectivities to methanol and dimethyl ether were 25% and 75% respectively.

EXAMPLE 7

Example 6 was repeated except that 0.68 g $Cu[(CH_3O)_3P]CF_3SO_3$ was used as the catalyst. The liquid sample taken at four hours showed a 30% conversion of methyl formate. The selectivity to methanol was 27% and to dimethyl ether 73%.

EXAMPLE 8

In this example, conditions were similar to that described in example 1 except 400 ml ethyl formate was used as the reactant in place of methyl formate. The reaction was carried out for four hours at which time the analysis showed an ethyl formate conversion of 66%. The selectivity to ethanol was 35% and 65% to diethyl ether.

EXAMPLE 9

An autoclave was charged with 300 ml n-butyl formate, 200 ml dioxane and 1.42 g methyl iodide. The autoclave was flushed with CO, then sealed and pressurized to 1 MPa with Co. The reactor was then heated to 210° C. and a solution of 0.48 g $Cu(CO)CF_3SO_3$ was pressurized into the autoclave with CO. The reaction was allowed to proceed for 1.5 hours at which time the products were analyzed indicating a 40% conversion of the butyl formate. The selectivity to butanol was 36% and 64% to dibutyl ether.

EXAMPLE 10

An autoclave was charged with 0.24 g $Cu(CO)CF_3SO_3$, 50 ml tetrahydrofuran and 50 ml 97% formic acid. The autoclave was flushed three times with helium, then heated to 180° C. for one hour. Analysis of the product showed a 43% conversion of the formic acid to CO and water. The selectivity of the reaction was a minimum of 99.5%.

This reaction was repeated at 210° C. with all other conditions being identical. The conversion of the formic acid in this case was 69% with no change in selectivity.

I claim:

1. A process for the homogeneous catalytic decarbonylation of formate esters of the formula HCOOR where R is $C_1-C_{10}$ aliphatic, $C_7-C_{14}$ araliphatic or $C_6-C_{10}$ aryl which comprises contacting the formate ester with a copper complex of the formula CU(L)X where L is CO, phosphine or phosphite and X is the anion of an acid in an inert atmosphere at temperatures of from about 100° to 300° C.

2. The process of claim 1 wherein R is $C_1-C_6$ alkyl.

3. The process of claim 1 wherein an iodide promoter selected from the group consisting of iodine, HI, alkali metal iodide, alkaline earth metal iodide, substituted and unsubstituted ammonium or phosphonium iodides and organic iodides is added.

4. The process of claim 3 wherein the organic iodide is a $C_1$–$C_{10}$ aliphatic iodide.

5. The process of claim 3 wherein the organic iodide is methyl iodide.

6. The process of claim 1 wherein the amount of copper complex is from 0.0001 to 1 wt. %, calculated as metal and based on the reaction mixture.

7. The process of claim 1 wherein an inert organic solvent is present as solvent.

8. The process of claim 1 wherein the inert atmosphere pressure is from about 0.1 to 100 MPa.

9. The process of claim 1 wherein the temperature is from 150° to 250° C.

10. The process of claim 1 wherein the L is CO, $P(OR')_3$ or $P(R')_3$ where R' is independently H, $C_1$–$C_{10}$ alkyl, $C_3$–$C_8$ cycloalky, $C_7$–$C_{14}$ aralkyl or $C_6$–$C_{10}$ aryl.

11. The process of claim 10 where L is CO or $P(OR')_3$.

12. The process of claim 1 where X is the anion of a strong acid.

13. The process of claim 1 where X is $CF_3SO_3^-$ or $CH_3C_6H_4SO_3^-$.

14. The process of claim 11 where R' is $C_1$–$C_{10}$ alkyl or phenyl.

15. The process of claim 1 wherein the copper complex is $CU(CO)CF_3SO_3$, $Cu(P(OCH_3)_3)$, $Cu(P(OC_6H_5)_3)CF_3SO_3$ or $Cu(CO)CH_3C_6H_4SO_3$.

16. A process for the homogeneous catalytic decarbonylation of formate esters of the formula HCOOR where R is $C_1$–$C_6$ alkyl which comprises contacting the formate ester with a copper complex of the formula Cu(L)X wherein L is CO, $P(OR')_3$ or $P(R')_3$ where R' is independently H, $C_1$–$C_{10}$ alkyl, $C_3$–$C_8$ cycloalkyl, $C_7$–$C_{14}$ aralkyl or $C_6$–$C_{10}$ aryl and X is the anion of a strong acid in an inert atmosphere at temperatures of from about 100° to 300° C.

* * * * *